(12) United States Patent
Thundat et al.

(10) Patent No.: US 7,716,965 B2
(45) Date of Patent: May 18, 2010

(54) ELECTROCHEMICAL SENSOR HAVING SUSPENDED ELEMENT COUNTER ELECTRODE AND DEFLECTION METHOD FOR CURRENT SENSING

(75) Inventors: Thomas G. Thundat, Knoxville, TN (US); Gilbert M. Brown, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 709 days.

(21) Appl. No.: 11/588,542

(22) Filed: Oct. 27, 2006

(65) Prior Publication Data

US 2008/0099330 A1 May 1, 2008

(51) Int. Cl.
*G01N 27/00* (2006.01)
(52) U.S. Cl. .............. 73/23.2; 422/83; 422/91; 422/52; 204/406; 204/407; 204/412; 204/416; 204/433; 204/435; 73/24.06; 436/163; 205/787.5; 205/789; 205/789.5; 205/793.5; 324/453
(58) Field of Classification Search .......... 204/406, 204/407, 412, 416, 433, 435; 73/23.2, 24.06; 422/52, 83, 91; 436/163; 205/787.5, 789, 205/789.5, 793.5; 324/453
See application file for complete search history.

(56) References Cited

U.S. PATENT DOCUMENTS 5,329,236 A * 7/1994 Gemma et al. .............. 324/453
6,016,686 A * 1/2000 Thundat ..................... 73/23.2
2005/0121615 A1* 6/2005 Prater et al. ................. 250/343
2005/0151530 A1* 7/2005 Shekhawat et al. ......... 324/71.1
2005/0244820 A1* 11/2005 Su et al. ....................... 435/5
2006/0191329 A1* 8/2006 Adderton et al. ............. 73/105
2006/0230817 A1* 10/2006 Schilowitz et al. ......... 73/53.01

OTHER PUBLICATIONS

Oden et al. "Electrochemical Deposition Induced Stress Measurements on a Microcantilever Investigated with Cyclic Voltammetry", Scanning Microscopy, (1998), vol. 12, No. 13, pp. 449-454.
Tabard-Cossa et al. "A Differential Microcantilever-Based System for Measuring Surface Stress Changes Induced by Electrochemical Reactions", Science and Actuators, (2005), B, vol. 107, pp. 233-241.

* cited by examiner

*Primary Examiner*—Bruce F Bell
(74) *Attorney, Agent, or Firm*—Novak Druce + Quigg LLP; Gregory A. Nelson; Gregory M. Lefkowitz

(57) ABSTRACT

An electrochemical suspended element-based sensor system includes a solution cell for holding an electrolyte comprising solution including at least one electrochemically reducible or oxidizable species. A working electrode (WE), reference electrode (RE) and a counter electrode (CE) are disposed in the solution. The CE includes an asymmetric suspended element, wherein one side of the suspended element includes a metal or a highly doped semiconductor surface. The suspended element bends when current associated with reduction or oxidation of the electrochemically reducible or oxidizable species at the WE passes through the suspended element. At least one measurement system measures the bending of the suspended element or a parameter which is a function of the bending.

14 Claims, 3 Drawing Sheets

ELECTROCHEMICAL SENSOR HAVING SUSPENDED ELEMENT COUNTER ELECTRODE AND DEFLECTION METHOD FOR CURRENT SENSING

STATEMENT REGARDING FEDERALLY SPONSORED RESEARCH OR DEVELOPMENT

The United States Government has rights in this invention pursuant to contract no. DEAC05-00OR22725 between the United States Department of Energy and UT-Battelle, LLC.

CROSS REFERENCE TO RELATED APPLICATIONS

N/A

FIELD OF THE INVENTION

The present invention relates to electrochemical sensors which include a suspended element (e.g. cantilever) electrode and a deflection-based method for sensing current.

BACKGROUND OF THE INVENTION

Microcantilever sensors are known to be excellent chemical and biological sensors. The Gibbs free energy of a surface is decreased by adsorption, and when molecular adsorption is confined to one surface of a microcantilever, this leads to differential surface forces between the two sides of the cantilever. When the spring constant of a microcantilever is of the same magnitude as the free energy change due to surface adsorption on it, the microcantilever undergoes deflection due to the adsorption-induced stress.

Microcantilever-based sensors have been shown to be extremely sensitive. However, microcantilevers coated on one surface with an electrical conductor (e.g. gold) do not provide chemical selectivity. A microcantilever coated on one surface with gold has achieved chemical selectivity by adsorbing a selection film on the gold coated side of the microcantilevers, such as a self-assembled monolayer (SAM) of an alkane thiol having a head group suitable for molecular recognition. Selective coatings have been developed for sensing a variety of different ions or other chemical species.

As an alternative to selective coatings, controlled potential electrochemical techniques provide a comparatively simple method for achieving chemical selectivity by controlling the potentials at which oxidation and reduction reactions occur. When using controlled potential electrochemical techniques, chemical selectivity is conventionally achieved using a cantilever coated on one surface with a metallic conductor as the working electrode.

The model of an electrified interface between an electrolyte solution and a conductor is well developed. Graham derived much of the understanding from seminal measurements of interfacial tension at an aqueous solution-mercury electrode interface. Investigations of surface stress during electrochemical processes have been reported for macro cantilevers and microcantilevers, but a rigorous description of the charge and potential dependence of the surface tension remains a challenge. These studies have demonstrated that the dependence of surface stress on charge and potential at the solid-electrolyte interface offer more insight into the processes occurring at an electrified interface in solution during electron transfer reactions and ionic adsorption processes.

Surface charge density and surface energy are related. Thermodynamics also provides a relationship between surface free energy, surface coverage, and surface stress. This relation can be differentiated with respect to potential to obtain the generalized Lippman equation that allows the derivative of surface stress with respect to potential to be related to the surface charge density during an electrochemical process.

In summary, the deflection of a microcantilever is proportional to the surface stress that is also related to the free energy change. Thus, the derivative of the surface stress with respect to electrical potential can be related to the surface charge density.

The differences between a cyclic voltammogram (current vs. potential) and surface stress variation with potential may provide insights into the physical and chemical processes, which accompany redox reactions at modified electrodes and additional information about changes in energetics at the solid-electrolyte interface. Such information could help in understanding double layers and diffusion layers in electrolyte solutions as well as changes which accompany charge transfer at the interface. The charge transfer effects are known to have a pronounced influence on the adsorbate-induced surface stress.

Although electrochemical cantilever-based sensors are presently useful for certain applications, the use of a microcantilever as the working electrode to date has revealed several significant limitations, including the following:

1) During prototyping of an electrochemical microcantilever sensor, it is generally necessary to carry out simultaneous measurement of electrochemical current and cantilever deflection so that the electrochemical reactions and other conditions of analysis are well defined.
2) Small spring constant cantilevers are required for high sensitivity. Accordingly, the surface area of a high sensitivity cantilever is kept extremely small, such as 100 µm by 10 µm, as compared to the much larger area of the base chip, and it is difficult to limit the area which is exposed to an analyte solution to the cantilever alone.
3) The current density that can be supported on a microcantilever is small due to the small surface area of the cantilever and measurement of the small current at an electrode with this surface area requires expensive amplifiers and special shielding to eliminate background electromagnetic interference.
4) When the cantilever is functioning as a working electrode its efficiency can decrease due to irreversible reactions that occur during use. Partial coverage of the cantilever surface by contaminants leads to poor cantilever performance due to a further decrease in the effective working surface area of the cantilever.
5) The materials that can be used on a cantilever as a working electrode are limited to those metals which can be deposited by an evaporation process at a temperature low enough to prevent damage to the cantilever itself, form an adherent layer on the cantilever, and at the same time are materials that are appropriate for electrochemical reactions in an aqueous environment. The materials that can be used as a working electrode are further limited since most cantilevers are fabricated out of silicon and coated with thin layers of specific metals. Coating cantilevers with metals brings in a variety of problem, including problems due to adhesion, crystalline nature, diffusion of other metals that are used as adhesion layers through the grain boundaries, and contamination. The materials that can be plated on one surface of a cantilever are thus generally limited to platinum and gold.

What is needed is an electrochemical cantilever-based sensor system that provides high sensitivity and overcomes the significant limitations of conventional electrochemical cantilever-based sensors noted above. It is also desirable to have electrochemical sensors that can be used in microfluidic applications in which a small surface area electrode is dictated by the confined geometry of the channels required by the application. In this case a small surface area electrode necessarily leads to small current levels. The measurement of small currents requires that the electrode be carefully shielded to prevent interference from electromagnetic radiation. This leads to a situation in which the advantages of small size brought by microfluidic devices, such as a lab-on-a-chip devices, are lost due to required electromagnetic shielding requirements which are incompatible with MEMS.

SUMMARY

An electrochemical suspended element-based sensor system includes a solution cell for holding an electrolyte comprising solution including at least one electrochemically reducible or oxidizable species. A working electrode (WE), reference electrode (RE) and a counter electrode (CE) are disposed in the solution. The CE includes an asymmetric suspended element, wherein one side of the suspended element includes a metal or a highly doped semiconductor surface. As used herein, the term "asymmetric suspended element" refers to a suspended element having a shape, composition or doping profile and/or coating(s) that results in bending of the suspended element when current passes through, such as when current associated with reduction or oxidation of the electrochemically reducible or oxidizable species at the WE passes through the suspended element. The sensor system also includes at least one measurement system to measure the bending/deflection of the suspended element or a parameter which is a function of the bending.

The measurement system can comprise an optical system for measuring the bending. In another embodiment, the CE comprises a piezoresistive material, wherein the measurement system comprising a circuit for measuring a resistance of the piezoresistive material, such as a Wheatstone Bridge.

The RE can also comprises a suspended element. In one embodiment, both the CE and the RE comprise cantilevers.

In a preferred embodiment, the system further comprises an integrated circuit substrate, wherein the solution cell, WE, RE, CE, and the measurement system components are disposed on the substrate (lab-on-a-chip). In this highly integrated embodiment, electronics including filters, amplifiers and a microprocessor can be integrated on the same substrate. Advantageously, current shielding is not required for measurement of small currents according to the invention, because as noted above the current data is derived from a measurable based on bending of the suspended element responsive to the current. In one embodiment, the substrate comprises silicon.

A method of identifying oxidizable or reducible species in solution comprises the steps of providing a solution cell holding an electrolyte comprising solution including at least one electrochemically reducible or oxidizable species, and a working electrode (WE), reference electrode (RE) and an asymmetric suspended element comprising counter electrode (CE) disposed in the solution, identifying the species in the solution based on measuring deflection of the CE or a parameter based on the deflection responsive to current associated with reduction or oxidation of the electrochemically reducible or oxidizable species at the WE passing through the suspended element. The method can further comprise the step of quantifying a concentration of the species in the solution. The identifying step can comprise optical detection of the deflection or when the CE comprises a piezoresistive material, the parameter based on deflection comprises an electrical resistance of the piezoresistive material.

The invention is not limited to electrochemical sensing. A method of measuring small electrical currents, comprises the steps of placing an asymmetric suspended element in a path of current to be measured, wherein one side of the suspended element includes a metal or a highly doped semiconductor surface, the suspended element bending when current flows therethrough, measuring the bending or a parameter which is a function of the bending, and determining a level of the current from the bending or the parameter which is a function of the bending. The measuring can comprise an optical method and when the suspended element includes piezoresistive material, the parameter can comprise a change in resistance of a piezoresistive material.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

Figure 1A:
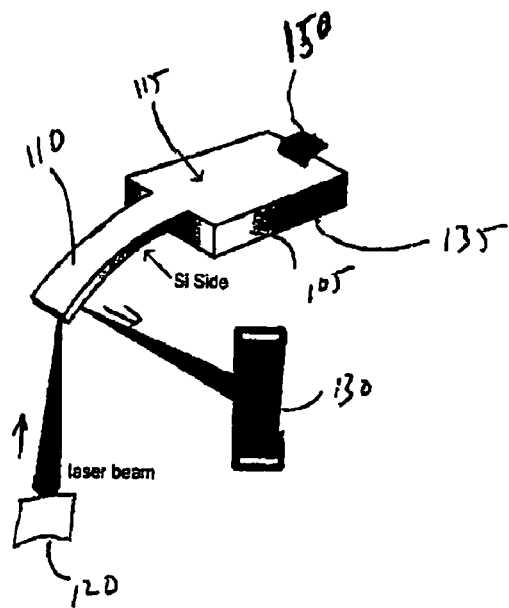
FIG. 1(a) shows a simplified representation of an optical system for measuring the deflection of a microcantilever counter electrode according to an embodiment of the invention which is formed on a chip.

An electrochemical suspended element-based sensor system includes a solution cell for holding an electrolyte comprising solution including at least one electrochemically reducible or oxidizable species. A working electrode (WE), reference electrode (RE) and a counter electrode (CE; also known as an auxiliary electrode) are disposed in the solution. The CE includes an asymmetric suspended element, wherein one side of the suspended element includes a metal or a highly doped semiconductor surface. The suspended element bends when current associated with reduction or oxidation of the electrochemically reducible or oxidizable species at the WE passes through the suspended element. At least one measurement system measures the bending/deflection of the suspended element or a parameter which is a function of the bending.

Although the invention is generally described relative to a three (3) electrode system, as known in the art, in certain cases a two (2) electrode system can be configured by using the CE as the RE. For example, the RE and CE can be combined if the composition of the CE is such that it is an ideally non-polarizable metal (e.g., Ag metal with an AgCl coating in a solution containing excess $Cl^-$ ions) which does not measurably change in potential with an increase in current.

As noted above, the suspended element bends when current associated with reduction or oxidation of the electrochemically reducible or oxidizable species at the WE passes through the electrically conductive side of the suspended element. Since bending of the CE in response to oxidation/reduction occurring on the WE or a parameter which is a function of the bending is measured rather than the current itself, as described below, the invention provides a more sensitive and more universal platform for electrochemical detection of species. Significantly, the present invention also eliminates the need for electrode shielding required by conventional systems to measure low current levels.

At least one suspended element-based measurement system is provided. The measurement system can comprise (i) an optical system for measuring deflection of the suspended element, or, when the CE includes a piezoresistive material as described below, (ii) an electrical system for measuring the electrical resistance (or current flowing through) the piezoresistive material varying as a function of bending the suspended element. A current measuring system for measuring the current associated with reduction or oxidation of the electrochemically reducible or oxidizable species can also be provided.

The electrochemical reaction taking place at the WE can result in thin film deposition, ion adsorption, or in a preferred embodiment of the invention produce any type of redox reaction on the WE surface. This reaction is compensated by current flow at the CE. Current thus flows between WE and CE. The presence of the RE provides an equilibrium reaction that determines the reference level in the electrochemical cell. An insignificant level of current flows through the RE.

In typical operation, a conventional potentiostat is connected to the WE, RE, and CE. The potentiostat includes electronic circuitry for controlling a voltage difference between the working electrode and reference electrode, applying a potential between the WE and the CE, and for monitoring the current response from the WE. In a typical process such as cyclic voltammetry, the potential of the WE is varied with respect to the RE in a linear ramp to a switching potential and reversed to the starting potential while the current is measured as a function of potential. As noted above, an optical beam technique can be used to monitor the deflection of the suspended element, provided the solution cell is optically transparent. In this case a function of cantilever deflection can be measured as a function of voltage to define the electrochemical process.

The present invention thus provides a new method for electrochemical or more generally low current sensing. Unlike present electrochemical sensing systems, systems according to the invention thus do not use a cantilever or suspended structure as the WE, do not require complex electronics, and can be more compact as compare to a conventional system in which only the current can be measured and requires extensive electromagnetic shielding and expensive current amplifiers.

The suspended element is generally described herein as being a cantilever element. Although a cantilever is supported with one supporting member such as a single post, the suspended element can be formed from any suspended structure that provides flexure under stress, such as a suspended element supported at multiple ends such as two ends, or supported across an entire circumference as in the case of a suspended diaphragm element.

Significantly, the WE of the present invention does not utilize a cantilever (or other suspended element). The WE instead is preferably an electrode of comparable area to the cantilever chip (base plus cantilever) which is exposed to solution and which can be comprised of either a metal or semiconductor surface.

Instead of the WE being a cantilever, the CE is a cantilever (or other suspended structure). Typical dimension of the cantilever can be 20-500 microns, 0.3 to 4 microns in thickness, and 5 to 50 microns in width. However, thinner and longer cantilevers can be used to provide higher deflection sensitivity due to their small spring constants.

The optical system implements the known optical beam deflection technique which monitors the deflection of a suspended element. A simplified representation of such an optical system is shown as system 100 in FIG. 1(a) for measuring the deflection of a microcantilever I 10 which is formed on chip 105. The surface of microcantilever 110 and chip 105 include an electrically conductive coating 115. Electrical contact is generally made on the topside of chip at clip 150. The optical system generally comprises a light source, such as laser 120 emitting a light beam aligned incident on the microcantilever 110. A photodetector 130 is aligned to receive light reflected from the microcantilever 110. All system components, including mirrors if required, can be formed on a common substrate (e.g. silicon chip) using standard MEMS processing.

The significance of MEMS technology is that it makes possible mechanical parts of micron size, such as solution cells, that can be integrated on a common substrate with optical devices such as lasers and mirrors, and electronic devices such as photodetectors and potentiostats, and batch fabricated in large quantities. MEMS devices are fabricated through the process of micromachining, a batch production process employing lithography. Micromachining relies heavily on the use of lithographic methods to create 3-dimensional structures using pre-designed resist patterns or masks. MEMS is one suitable technology for making microfabricated devices or aspects thereof. Microfabricated devices are generally defined as devices fabricated by using MEMS and/or integrated circuit (IC) technology. An IC is defined as a tiny chip of substrate material (e.g. silicon) upon which is etched or imprinted a complex of electronic components and their interconnections.

The exemplary microcantilever 110 can be made from polysilicon and is presently commercially available within limited dimensions. Electrically conductive coating 115 can be a metal (e.g. gold or silver layer) or highly doped semiconductor layer.

The microcantilever 110 can also be a thin metal film with same dimensions as described above, but with a coating of an electrically insulating material on one side. In another alternate embodiment, the microcantilever 110 can also be a thin semiconductor with highly doped upper side and undoped or lightly doped bottom side.

The deflection of the microcantilever can also be measured indirectly by use of a piezoresistive comprising microcantilever. As known in the art, the piezoresistive effect describes changing electrical resistance of a material due to applied mechanical stress. This embodiment uses electronic components and does require optical components.

Figure 1B:
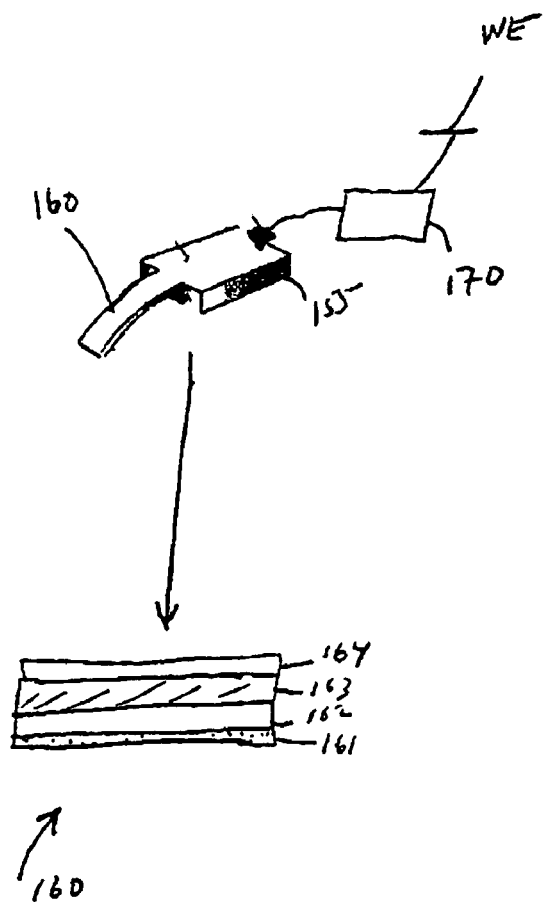
FIG. 1(b) shows a representation of a piezoresistive comprising microcantilever than can be used as a CE for electrically monitoring the CE deflection coupled to a circuit for measuring the resistance of the piezoresistive element.

FIG. 1(b) shows a representation of a piezoresistive comprising microcantilever 160 than can be used as a CE for electrically measuring the deflection when coupled with electrical measurement circuit 170. Microcantilever 160 is formed on chip 155. An expanded view of the various layers comprising microcantilver 160 is also shown in FIG. 1 (b). In this embodiment, the CE suspended structure 160 comprises a piezoresistive material wherein the electrical resistance of the piezoresistive material varies sensitively as a function of bending of the suspended structure. Materials such as certain metals, and semiconductors including germanium, polycrystalline silicon, amorphous silicon, silicon carbide, and single crystal silicon are known to exhibit piezoresistivity. As known in the art, piezoresistive structures can be made by asymmetric doping of a semiconducting material with respect to the neutral axis of bending of the structure.

For example, piezoresistive structures according to the invention can be made by coating a base microcantilever 162 (such as formed from undoped polysilicon) material so that the thickness of the a piezoresistive coating 163 is higher on one side of the suspended element than its other side such that the neutral axis of bending will be inside the thickness of the coating. Doped silicon can be the piezoresistive layer 163 and optional electrically insulating material 161 can be silicon nitride or silicon dioxide. The coating material used is electrically insulating and does not take part in electrochemical reactions. The topside 164 of microcantilever 160 is coated with a metal or other highly electrically conductive material for applying potential between the microcantilever CE 160 and the WE.

In operation, a piezoresistive electrical measurement circuit 170, such as a Wheatstone Bridge, measures an electrical resistance of the piezoresistive comprising microcantilever CE 160, which varies as microcantilever CE 160 bends responsive to current passing through. Measurement circuit 170 is generally independent of the electrochemical circuit (potentiostat) of the electrochemical system (not shown).

Figure 2:
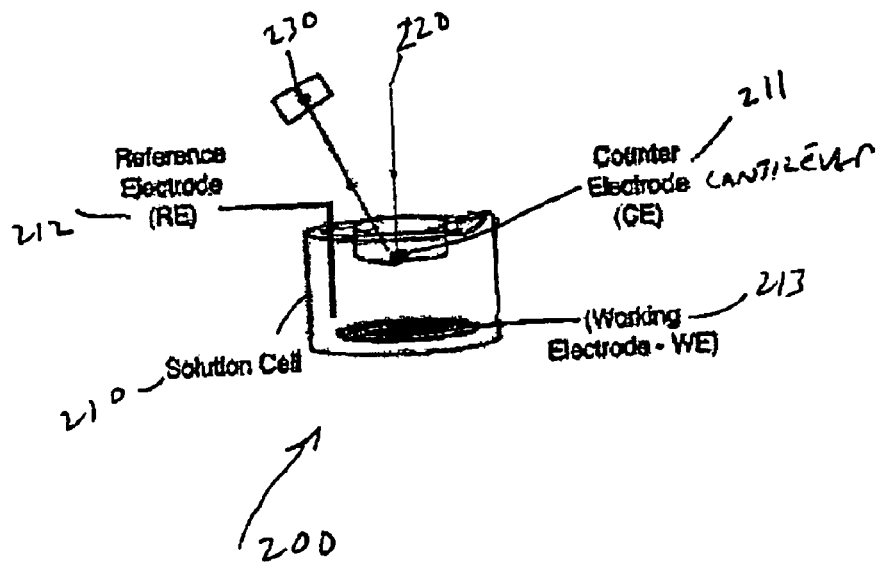
FIG. 2 shows a view of a system including an electrochemical cell and optical deflection measurement system that can be used with the invention.
Figure 2:
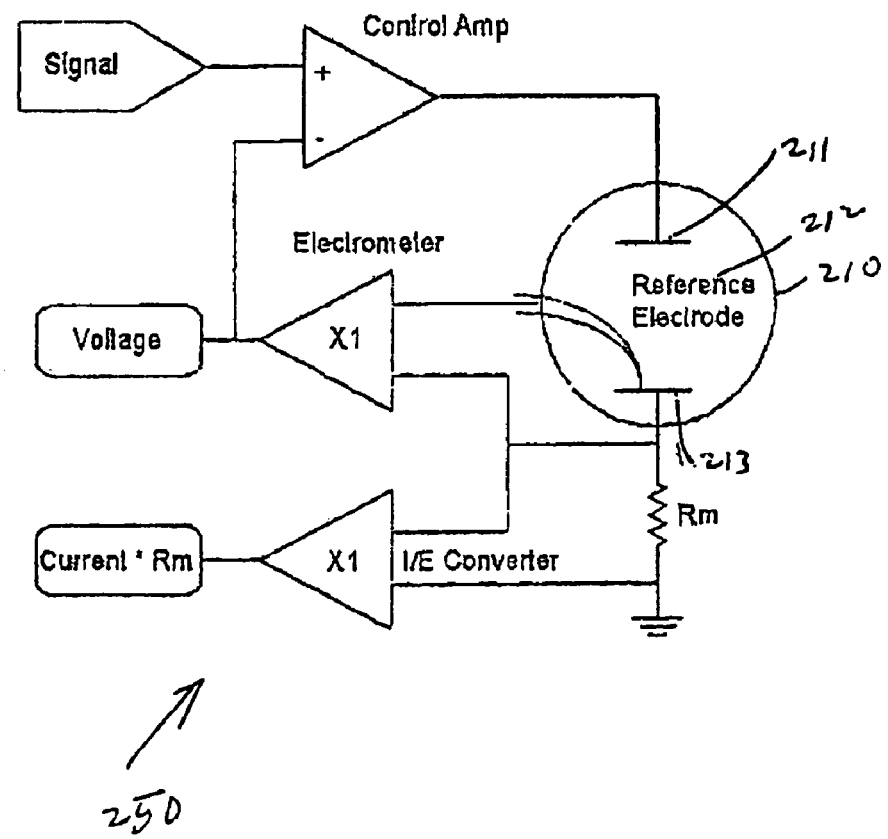

FIG. 2 shows a view of a system 200 including an electrochemical cell and optical deflection measurement system that can be used with the invention. A RE 212 and WE 213 are also disposed in the solution held within a solution cell 210. Optical deflection measurement system comprises laser 220 emitting a light beam aligned incident on the microcantilever CE 211. A photodetector 230 is aligned to receive light emanating from the microcantilever 211. A conventional potentiostat is shown below system 200 connected to CE 211, RE 212 and WE 213.

The solution cell 210 includes an optically transparent portion (glass) to accommodate the preferred optical beam deflection scheme. In one embodiment, the entire solution cell is formed from an optically transparent material.

Potentiostat 250 is a well-known electronic device that uses several operational amplifiers to control the voltage difference between the WE 213 and the RE 212. The potentiostat implements this voltage control by injecting current into the cell between the CE and the WE. The CE thus completes the cell circuit. In all controlled potential applications, the potentiostat 250 measures the current flow between the WE and CE, and this is the quantity that is dependent on the concentration of analyte in solution.

The CE cantilever thus bends when current associated with the electrochemical reaction occurring at the WE passes through the CE cantilever. This is mainly due to the differential surface charge density developed. The CE cantilever bends due to extremely small changes in charge density (differential charge density) resulting from current flow. Accordingly, the invention can be used to detect extremely small currents by detecting cantilever bending using optical or piezoresistive detection-based methods without using complicated potentiostat electronics or electromagnetic shielding to determine extremely small current flow.

Figure 3:
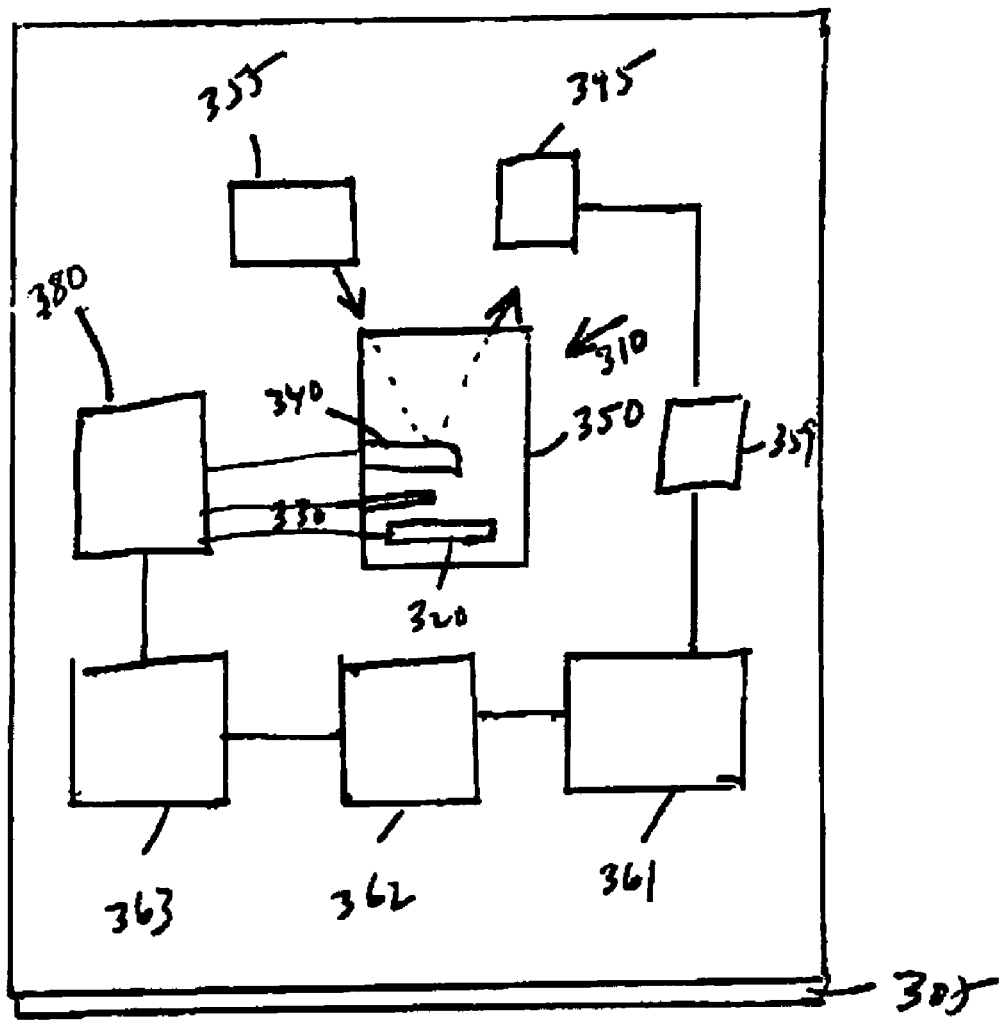
FIG. 3 is a schematic of electrochemical sensor system on a chip having its respective components all integrated on a substrate, according to an embodiment the present invention.

FIG. 3 is a schematic of electrochemical sensor system on a chip 300 having its respective components all integrated on a substrate 305, according to an embodiment the present invention. The sensor 310 comprises a WE 320, a RE 330 and a CE 340 fabricated on a substrate 305. Preferably, the electrodes are all made out of gold. The WE 320 is formed in a built-in well 350 in the substrate having a depth of up to about 300 μm. The well 350 is designed for confining a desired solution within the well-defined volume provided. Well 350 can be fabricated using standard microfabrication methods and can be bordered by (111) silicon planes after KOH etching when substrate 305 comprises silicon.

Potentiostat 380 is electrically coupled to WE 320, RE 330 and a CE 340 in a conventional arrangement. Potentiostat 380 can be an analogous design having analogous electrode connections as those shown relative to potentiostat 250 shown in FIG. 2. Light source 355, such as a laser, LED, or other collimated beam of light, is aligned to direct light to the CE 340. Light reflected from CE 340 reaches photodetector 345, such as a photodiode, avalanche diode or phototransistor which outputs an electrical signal. Low pass filter 359 removes high frequency noise and amplifier 361 amplifies the filtered signal. The signal is digitized by A/D converter 362 and then provided to microprocessor 363. Microprocessor is also communicably connected to potentiostat 380.

Microprocessor preferably has associated data storage on chip, including calibration data comprising bending as a function of current though the suspended element in the case of optical-based detection and resistance change as a function of current through the suspended element in the case of piezoresistive-based detection. Calibration data is typically generated for a given solution mixture using available highly shielded and complex conventional electronics for measuring the current.

A method of identifying electrochemically active species according to the invention comprises the steps of providing a solution cell holding an electrolyte comprising solution including at least one electrochemically reducible or oxidizable species, and a WE, RE and suspended element comprising CE disposed in the solution. Electrochemically active species in the solution are identified and quantified based on a deflection of the suspended element comprising CE responsive to current associated with reduction or oxidation of the electrochemically reducible or oxidizable species at the WE passing through the suspended element. Identification and quantification generally comprises reference to calibration data as described above.

The cantilever deflection as a function of sweeping electrode potential will be similar to that of an ordinary voltammogram (current vs. sweeping potential). Peaks in cantilever bending as a function of sweeping potential show increased electron flow and thus indicate electrochemical reactions occurring that WE. Since the double layer around the cantilever is charging (discharging) during the potential sweep, the deflection of the cantilever changes monotonically, and the peaks due to electrochemical reactions occur on top of the bending due to double layer charging. Therefore, a differential of the bending curve with respect to sweeping voltage can be used for clarity.

The potential at which the electrochemical reactions occur depends on the nature of the electrochemically active species. As the potential between the CE and WE is changed, the Fermi level of the electrode and the electrochemical potential of the electrochemically active species in the solution reaches the isoelectronic which causes electron transfer. Different electrochemically active species are readily identified by their characteristic electrochemical potentials which creates currents at different values of applied potential. The concentration of the electroactive species is proportional to the current flow as measured by cantilever deflection.

As described above, the present invention is ideally suited for application to electrochemical sensing systems for detection of ions and other electroactive species. The invention is expected to have particular utility as the detection element in microfluidic and lab-on-a-chip applications requiring the measurement of small currents (nA to pA) where a small discrete inexpensive detection system is desired. However, the current sensing aspect of the present invention can be embodied in a variety of systems beyond electrochemical sensing systems.

The invention more generally provides a method of measuring small electrical currents. This method comprises the steps of placing an asymmetric suspended element in a path of current to be measured, wherein one side of the suspended element includes a metal or a highly doped semiconductor surface. The suspended element bends when current flows therethrough. The degree of bending or a parameter which is a function of the bending (piezoresistance) is measured. The level of current flowing is then determined from the bending or the parameter which is a function of the bending generally using calibration data as described above.

For example, the invention can be embodied as a mechanical ammeter which quantifies current flow based on current induced mechanical movements. This can be achieved by for example, creating a potential difference across a resistor inserted in series in the current carrying element and connecting a metal plate-air-cantilever in parallel with the resistor. Current flow in the system creates a voltage drop across the resistor that will be same as the voltage drop across the cantilever-air-metal plate arrangement. The voltage creates a surface charge density on the metal plate. The charge density on the metal plate results in cantilever bending. The extent of cantilever bending is proportional to the current flowing in the system. The cantilever bending changes when current in the system changes. Unlike in the solution where the distance between the cantilever and the solution can be large, in this case the distance between the cantilever and the metal plate should be extremely small. The gap between the metal electrode and the cantilever can be air or other dielectric.

Another exemplary application for current sensing according to the invention is a system for detecting ionizing radiation. In operation, a large electrical potential is applied between a capacitor comprising a cantilever (e.g. +) and a metal plate (e.g. −) separated by a dielectric gas. A plurality of cantilevers can be provided. Ionizing radiation causes both positive and negative ion generation in the dielectric gas. Such ions are electrostatically attracted to the oppositely charged electrodes resulting in a very small current in the system which is detected based on bending of the suspended element using optical or piezoresistive-based methods as described above.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. An electrochemical suspended element-based sensor system, comprising:
   a solution cell holding an electrolyte comprising solution including at least one electrochemically reducible or oxidizable species;
   a working electrode (WE), reference electrode (RE) and a counter electrode (CE) disposed in said solution, said CE comprising an asymmetric suspended element, wherein one side of said suspended element includes a metal or a highly doped semiconductor surface, said suspended element bending when current associated with reduction or oxidation of said electrochemically reducible or oxidizable species at said WE passes through said suspended element,
   a potentiostat, and
   at least one measurement system for measuring bending of said suspended element or a parameter which is a function of said bending, wherein said working electrode, said counter electrode and said reference electrode are operably connected to said potentiostat.

2. The system of claim 1, wherein said measurement system comprises an optical system for measuring said bending.

3. The system of claim 1, wherein said CE comprises a piezoresistive material, an electrical resistance of said piezoresistive varying as a function of said bending, said measurement system comprising a circuit for measuring a resistance of said piezoresistive material.

4. The system of claim 1, wherein said RE comprises a suspended element.

5. The system of claim 4, wherein said CE and said RE comprise a cantilever.

6. The system of claim 1, further comprising an integrated circuit substrate, wherein said solution cell, said WE, said RE, said CE, and said measurement system are disposed on said substrate.

7. The system of claim 1, wherein said substrate comprises silicon.

8. A method of identifying oxidizable or reducible species in solution, comprising the steps of:
   providing a solution cell holding an electrolyte comprising solution including at least one electrochemically reducible or oxidizable species, and a working electrode (WE), reference electrode (RE) and an asymmetric suspended element comprising counter electrode (CE) disposed in said solution;
   identifying said species in said solution based on measuring deflection of said CE or a parameter based on said deflection responsive to current associated with reduction or oxidation of said electrochemically reducible or oxidizable species at said WE passing through said suspended element.

9. The method of claim 8, further comprising the step of quantifying a concentration of said species in said solution.

10. The method of claim 8, wherein said identifying step comprises optical detection of said deflection.

11. The method of claim 8 wherein an electrical measurement circuit is coupled to said CE, said CE comprising a piezoresistive material, an electrical resistance of said piezoresistive material varying as a function of said bending, wherein said parameter based on said deflection comprises an electrical resistance of said piezoresistive material.

12. A method of measuring small electrical currents, comprising the steps of:
   placing an asymmetric suspended element comprising counter electrode (CE) in a path of current to be measured,
   wherein one side of said suspended element includes a metal or a highly doped semiconductor surface, said suspended element bending when current flows therethrough,
   measuring said bending or a parameter which is a function of said bending, and
   determining a level of said current from said bending or said parameter which is a function of said bending.

13. The method of claim 12, wherein said measuring comprises an optical method.

14. The method of claim 12, wherein said suspended element comprises a piezoresistive material, an electrical resistance of said piezoresistive varying as a function of said bending, said parameter comprising a change in resistance of a piezoresistive material.

* * * * *